United States Patent
Durbin et al.

(10) Patent No.: US 6,364,660 B1
(45) Date of Patent: Apr. 2, 2002

(54) METHOD AND SYSTEM FOR IMAGING AND MODELING DENTAL STRUCTURES

(76) Inventors: Duane Milford Durbin, 7660 Norcanyon Way, San Diego, CA (US) 92126; Dennis Arthur Durbin, 711 Marsolan, Solana Beach, CA (US) 92075

( * ) Notice: Subject to any disclaimer, the term of this patent is extended or adjusted under 35 U.S.C. 154(b) by 0 days.

(21) Appl. No.: 09/696,065

(22) Filed: Oct. 25, 2000

(51) Int. Cl.[7] ................................................ A61C 5/00
(52) U.S. Cl. ......................... 433/29; 433/213; 433/214
(58) Field of Search ............................. 433/25, 29, 68, 433/213, 214, 215, 223; 364/468.04, 474.05, 474.24

(56) References Cited

U.S. PATENT DOCUMENTS

| | | | | |
|---|---|---|---|---|
| 3,861,044 A | * | 1/1975 | Swinson, Jr. | |
| 4,324,546 A | * | 4/1982 | Heitlinger et al. | 433/25 |
| 4,575,805 A | * | 3/1986 | Moermann et al. | 364/474 |
| 4,611,288 A | * | 9/1986 | Duret et al. | 364/474 |
| 4,935,635 A | * | 6/1990 | O'Harra | 250/560 |
| 5,115,307 A | * | 5/1992 | Cooper et al. | 358/98 |
| 5,359,511 A | * | 10/1994 | Schroeder et al. | 364/413.28 |
| 5,372,502 A | * | 12/1994 | Massen et al. | 433/215 |
| 5,401,170 A | * | 3/1995 | Nonomura | 433/173 |
| 5,545,039 A | * | 8/1996 | Mushabac | 433/215 |
| 5,587,912 A | * | 12/1996 | Andersson et al. | 364/468.04 |
| 5,857,853 A | * | 1/1999 | Van Nifterick et al. | 433/213 |
| 6,126,445 A | * | 10/2000 | Willoughby | 433/223 |

* cited by examiner

*Primary Examiner*—Ralph A. Lewis

(57) ABSTRACT

A system optically images a dental structure within an oral cavity. The system includes an intra-oral track adapted to be inserted inside the oral cavity; an image aperture movably coupled to the intra-oral track and adapted to capture one or more images of the dental structure; and an image processor coupled to the image aperture to generate a three-dimensional (3D) model of the dental structure based on the images captured by the image aperture.

25 Claims, 6 Drawing Sheets

METHOD AND SYSTEM FOR IMAGING AND MODELING DENTAL STRUCTURES

FIELD OF INVENTION

The present invention relates to intra-oral methods and apparatus for optically imaging a dental structure and creating representative 3D models from the images.

BACKGROUND

In many dental applications, a working model of a patient's teeth is needed that faithfully reproduces the patient's teeth and other dental structures, including the jaw structure. Conventionally, a three-dimensional negative model of the teeth and other dental structures is created during an impression-taking session where one or more U-shaped trays are filled with a dental impression material. Impression materials include, among others, compositions based on alginates, polysulphides, silicones and vulcanizable polyether materials. The impression material is typically prepared by mixing a base component and a hardener or initiator or catalyst component. The impression tray containing the impression material, in its plastic state, is introduced into the mouth of the patient. To ensure a complete impression, an excessive amount of impression material is typically used. While the tray and impression material is held in place, the material cures, and after curing, the tray and material are removed from the mouth as a unit. The impression material is allowed to solidify and form an elastic composition, which is the negative mold after removal. The working model is obtained by filling this impression with a modeling material.

Dental patients typically experience discomfort when the dentist takes an impression of the patient's teeth. The procedure can be even more uncomfortable for the patient if the impression materials run, slump or are otherwise expelled into the patient's throat. Such situations can potentially cause a gag reflex reaction from the patient. In addition to patient discomfort, the impression process is time consuming. Additionally, the impression process can be error-prone. For example, when the impression material is not properly applied, the resulting working model may not accurately reflect features on the teeth. Moreover, the model can show air bubbles trapped during the impression taking session. Depending on the accuracy required, such working model may not be usable and additional dental impressions may need to be taken. Further, the mold and working model are fragile and can be easily damaged. The need to store the fragile models for future reference tends to become a logistical problem for a dental practice as the number of archived models accumulates.

Automated scanning techniques have been developed as alternatives to the mold casting procedure. Because these techniques can create a digital representation of the teeth, they provide the advantage of creating an "impression" that is immediately transmittable from the patient to a dental laboratory. The digital transmission potentially diminishes inconvenience for the patient and eliminates the risk of damage to the mold. For example, U.S. Pat. No. 6,050,821 discloses a method and apparatus for intra-orally mapping the structure and topography of dental formations such as peridontium and teeth, both intact and prepared, for diagnosis and dental prosthetics and bridgework by using an ultrasonic scanning technique. As claimed therein, the method can provide details of orally situated dental formations thus enabling diagnosis and the preparation of precision moldings and fabrications that will provide greater comfort and longer wear to the dental patient. Also, as discussed therein, infra-red CAD/CAM techniques have been used to map impressions of oral structures and make single-tooth prosthetics.

SUMMARY

In one aspect, a method for optically imaging a dental structure within an oral cavity by capturing one or more images of the dental structure through at least one image aperture, the image aperture movably coupled to an intra-oral track; and generating a three-dimensional (3D) model of the dental structure based on the images captured through the image aperture.

Implementations of the above method may include one or more of the following. The image aperture may be moved incrementally or continuously within the oral cavity. A motor can be actuated to move the image aperture incrementally or continuously within the oral cavity. The intra-oral track is arch-shaped. An illuminator can be movably mounted on the intra-oral track to illuminate the dental structure. The illuminator can be moved incrementally or continuously within the oral cavity. The generation of the three-dimensional model can include performing a stereometric analysis on the captured images. The 3D generation can include performing scanning illumination beam and triangulation analysis on the captured images. The method includes displaying a representation of said 3D model and transmitting the 3D model over a network. The 3D model can be used for diagnosis and treatment of a patient.

In another aspect, a system optically images a dental structure within an oral cavity with an intra-oral track adapted to be inserted inside the oral cavity; at least one image aperture movably coupled to the intra-oral track and adapted to capture one or more images of the dental structure: and an image processor coupled to the image aperture to generate a three-dimensional (3D) model of the dental structure based on the images captured by the image aperture.

Implementations of the above aspect may include one or more of the following. The image aperture is either incrementally or continuously moved on the track. A motor can be coupled to the image aperture to move the image aperture incrementally or continuously within the oral cavity. One or more illuminators can be movably mounted on the intra-oral track to illuminate the dental structure. Each illuminator is incrementally or continuously moved within the oral cavity. The image processor can be a stereometric processor. The image processor can scan an illumination beam and perform triangulation analysis on the captured images to generate a three-dimensional model. A display can be coupled to the image processor to show a representation of said 3D model. The image processor can be coupled to a network to transmit the 3D model to a remote system. A camera can be connected to the image aperture. The camera can be intra-orally mounted or can be mounted outside of the oral cavity.

In yet another aspect, a system optically images a dental structure within an oral cavity with an intra-oral track adapted to be inserted inside the oral cavity; a plurality of image apertures movably coupled to the intra-oral track and adapted to capture one or more images of the dental structure; and an image processor coupled to the image apertures to generate a three-dimensional (3D) model of the dental structure based on the images captured by the image apertures.

Advantages of the system may include one or more of the following. The system provides automated intra-oral scanning of all the dental structures in the jaw through an optical aperture and combines the information available in the entire set of images to create and present an accurate 3D model of the scanned structures. The system allows intra-oral images of dental structures to be taken rapidly and with high resolution such that the acquired images can be processed into accurate 3D models of the imaged dental structures. The images and models can be used in dental diagnosis and used for the specification and manufacture of dental prosthetics such as bridgeworks, crowns or other precision moldings and fabrications. In addition, the system produces 3D models useful in the diagnosis and treatment planning process for dental malocclusions. The system-produced data representing a set of dental images and models can be transmitted electronically to support activity such as professional consultations or insurance provider reviews, and the images and models may be electronically archived for future reference.

The digital 3D model of patient's teeth and other dental structures has advantages over a conventional physical model due to the following: 1) 3D model efficiently created in a single step with accuracy meeting or exceeding the conventional multiple step impression technique; 2)reduced storage costs; 3) immediate, labor-free retrieval and archiving; 4) no model breakage; 5) integrates directly into computer based analysis tools for diagnosis and treatment planning; 6) digital models backup; 7) e-mails to colleagues, dental specialists, insurance companies; 8) access to information from home, satellite office: 9) effective presentation tool; 10) no mess and dust; and 11) no wasted staff time.

The above and other features and advantages of the present invention will be apparent in the following detailed description of the preferred embodiments of the present invention when read in conjunction with the accompanying drawings in which corresponding parts are identified by the same reference symbol.

DESCRIPTION

Figure 1:
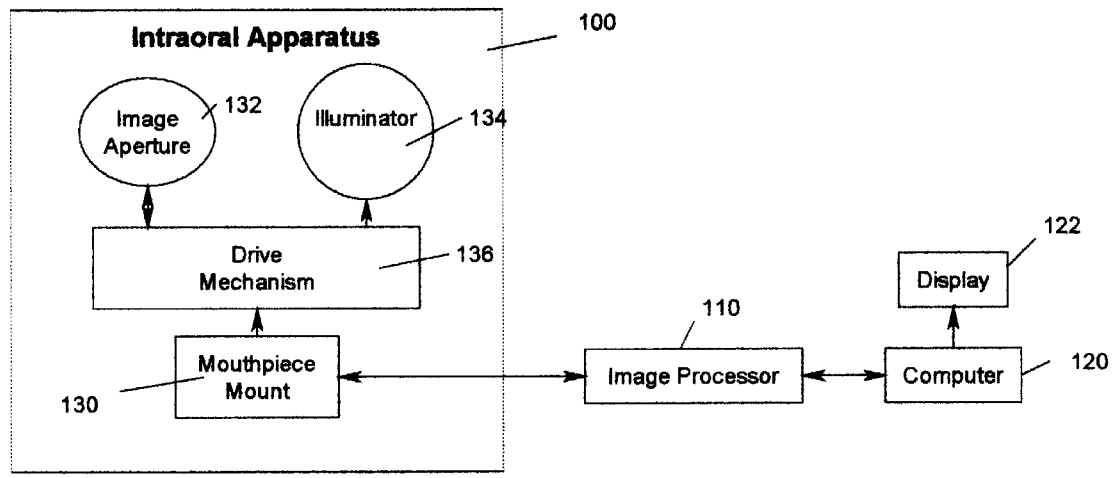
FIG. 1 illustrates an embodiment of a system for performing intra-oral scanning and for generating 3D models of teeth and other dental structures.

Referring to FIG. 1, a system block diagram depicting the instrumentation used in scanning teeth and other dental structure images and in generating 3D models, will facilitate a general understanding and appreciation of the disclosed method and apparatus.

In FIG. 1, an intra-oral scanner 100 is adapted to be placed inside the mouth of the patient (intra-oral cavity). The intra-oral scanner 100 captures images of various dental structures in the mouth and communicates this information with a remote image processor 110. The remote image processor 110 in turn can communicate with a computer 120 and can display images of the dental structures on a display 122 connected to the computer 120. Alternatively, functionalities of the computer 120 such as data storage and display can be provided directly by the remote image processor 110 in another embodiment. Images and 3D models derived from the images can be transmitted as digital files to other equipment or locations by the computer 120.

In one implementation, the intra-oral scanner 100 is embedded in an intra-oral structure, such as a mouthpiece 130. An image aperture 132 is provided to capture images of the dental structures. The image aperture 132 can be an objective lens followed by relay lens in the form of a light-transmission cable such as a fiber optic cable to transmit images of the dental structures along a pre-selected distance to a camera. The fiber optic cable transmits light through small filamentary optical materials or fibers. Typically, the fibers include a central core and an outer surrounding cladding along the entire length of the fiber. The transmission of light through the fiber is based on the phenomenon of total internal reflection. For total internal reflection, the refractive index of the core is greater than the refractive index of the cladding. In one embodiment, optical fibers for the transmission of images comprised of visible through mid-infrared light can be used.

The output of the image aperture 132 can be provided to one or more sensors for detecting and converting incident light (photons from the light source reflected off the dental structure surface)—first into electronic charge (electrons) and, ultimately into digital bits. In one implementation, the output of the image aperture 132 is provided to a camera (not shown), which can be analog or digital. In one embodiment, the camera contains one or more image sensor(s) used to create digital images of the dental structure. These sensors can be devices such as a charge-coupled device (CCD) sensor or a complementary metal oxide semiconductor (CMOS) image sensor. The image sensor can be an array of individual photosensitive cells (pixels) whose size determines the limiting resolution. Image sensor arrays can have from 16×16 pixels to more than 1024×1024 pixels and the arrays can be symmetrical or asymmetrical.

Further, a source of light delivered through an illuminator 134 is provided to illuminate the dental structures to improve the quality or contrast of the images taken by the image aperture 132. The light can be white light, light shown in one or more colors, or can come from a laser beam. The intensity of the light source used to illuminate the dental structure is ideally controllable and is in the frequency range of visible or infra-red light. In one embodiment, the light source can be integral to the mouthpiece 130. In another embodiment, light can be routed from the light source to the illuminator 134 by one or more fiber optic cables (not shown). This bundle of optical fibers can be positioned to surround the outer circumference of the image aperture 132 to create a plurality of illuminators. The field of illumination may be greater than the field of view of the image aperture 132 and may range up to 180 degrees. In another embodiment, the field of illumination may be a focused beam that illuminates a spot on the dental structure with an illumination spot size of dimensions less than 5 mm.

A drive mechanism 136 is provided to incrementally or continuously move the image aperture 132 and the illuminator 134 to various positions in the intra-oral cavity. In one embodiment, the image aperture 132 and the illuminator 134 are movably mounted on a track that is driven by the drive mechanism 136. The track can be a U-shaped track conforming to the shape of the patient's arch. The drive mechanism 136 can be electrically actuated to move the image aperture 132 and the illuminator 134 around all teeth and other structures in the jaw. Any of a variety of drive motors can be used, and the power of the motor through the drive mechanism 136 can be translated into motion for the image aperture 132 and the illuminator 134 through rotary, linear, hydraulic, or pneumatic mechanisms for example.

Figure 2:
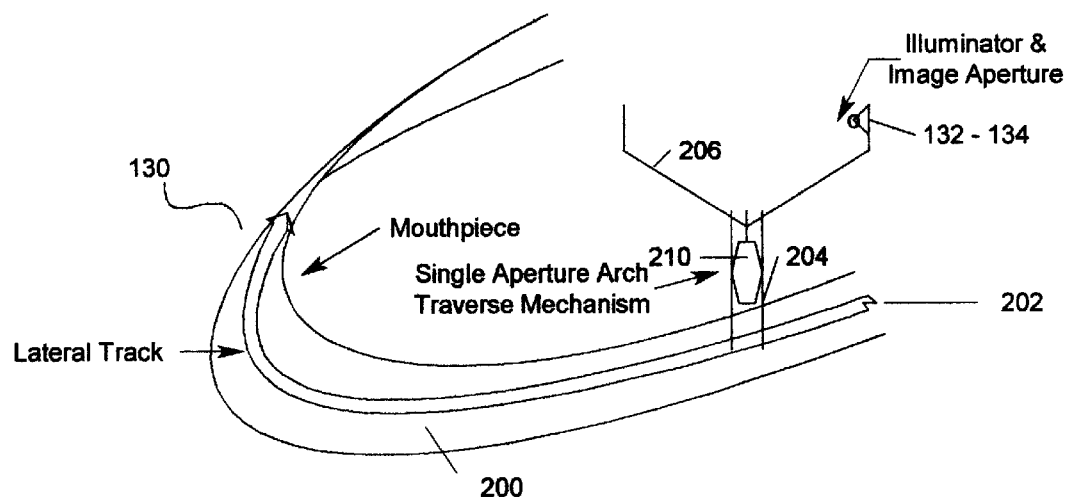
FIG. 2 shows an exemplary embodiment of a scanner with one aperture.

The intra-oral apparatus, as exemplified by mouthpiece 130, provides the mechanism for traversing image aperture 132 and the illuminator 134 around the oral cavity and positioning the image gathering aperture(s) 132A and illuminator(s) 134 at known positions while taking images of the dental structures. The mouthpiece 130 in one embodiment includes a sensor arc track 210 that allows the image aperture to traverse an arc to capture the image of the dental structure while also moving laterally (FIG. 2). In another embodiment, the mouthpiece 130 supports multiple image gathering apertures in known mechanical alignment and moving of said apertures laterally around the oral cavity (FIG. 3).

Although the scanning of one jaw arch at a time has been described, it is to be understood that two mouthpieces can be simultaneously deployed to capture images of dental structures on both the upper and lower jaw arches.

FIG. 2 shows one embodiment of the mouthpiece having a single image aperture. In the embodiment of FIG. 2, the mouthpiece 130 has a base 200 that is shaped substantially in an arch-shape or U-shape. Mounted on the base 200 is a lateral rail or track 202 that also conforms to the arch shape or U-shape. The track 202 supports a movable shuttle 204 driven by the drive mechanism 136. The shuttle 204 has an upwardly extending arm 206. Resting on top of the arm 206 are the image aperture 132 and the illuminator 134 of FIG. 1. Additionally, the arc track 210 allows the arm 206 to move from a frontal to a posterior view of the teeth. At each lateral position, the image aperture 132 traverses the arc track 210 over the dental structure to collect a sufficient number of images on both sides of the dental structure before moving to the next lateral position and repeating the process. The track 202 also includes sensors or indicators such as scale marks located at either end of the track 202 and along the track to provide image aperture positional feedback information. Alternatively, positional information can be ascertained by methods such as counting drive motor revolutions and deducing the position based on counting motor revolutions.

Figure 3:
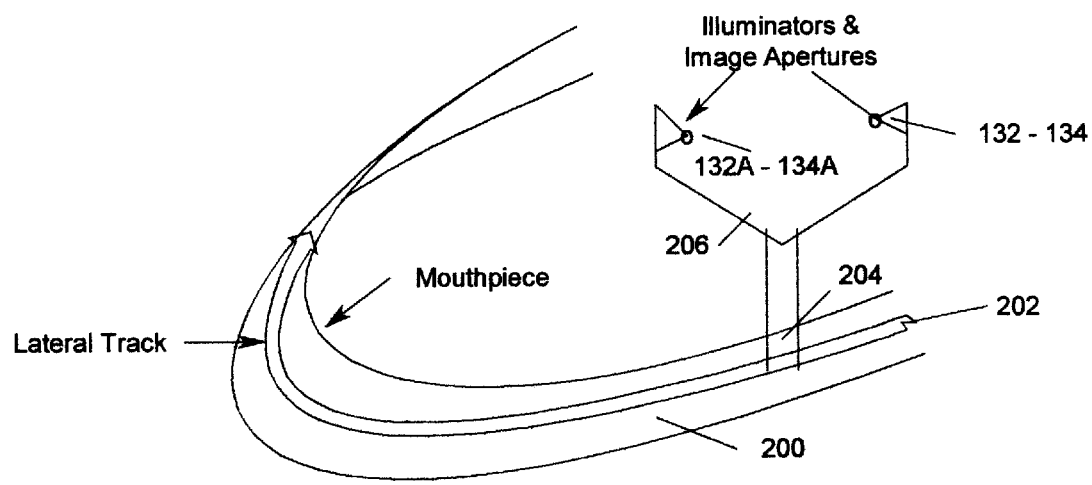
FIG. 3 shows a second embodiment of a scanner with a plurality of apertures.

FIG. 3 shows another embodiment with multiple image apertures that require only lateral motion. In this embodiment a plurality of image apertures 132A and the illuminator (s) 134A are mounted in a known orientation to one another on a laterally moveable apparatus. The number of image apertures and their orientation is selected to provide sufficient coverage and overlap of the dental structure to be modeled at the desired resolution. At each lateral position, an image from each of the apertures 132A is recorded for later processing. In either embodiment of FIG. 2 or FIG. 3, the image apertures 132 or 132A may be sensors integral to the mouthpiece or fiber optic image bundles connected directly to the mouthpiece. In the latter case, the fiber optic image bundle transmits the image to the image sensor on an external printed circuit board (PCB). To optimize the image collection at the image aperture, optical lenses may be employed to focus the image onto the image sensor.

As discussed above, the intra-oral scanner 100 contains components that support one or more of the following functions: 1) illuminate the dental structure to be imaged; 2) digitally image a dental structure from different aspects; and 3) reposition both the illumination and imaging apertures so as to traverse the entire intraoral cavity.

The intra-oral scanner 100 can be self-powered or power can be provided by the image processor 110. Further, the output of the intra-oral scanner 100 is received and processed by the image processor 110. In one embodiment the output of the scanner 100 includes images transmitted through a fiber optic cable. These images are provided to a camera that digitizes the images and stores the digital images in a memory buffer. In a second embodiment, the output of the scanner 100 is already in digital form, and this data is stored in the memory buffer of the image processor 110 for processing, as described in more detail below.

Figure 4:
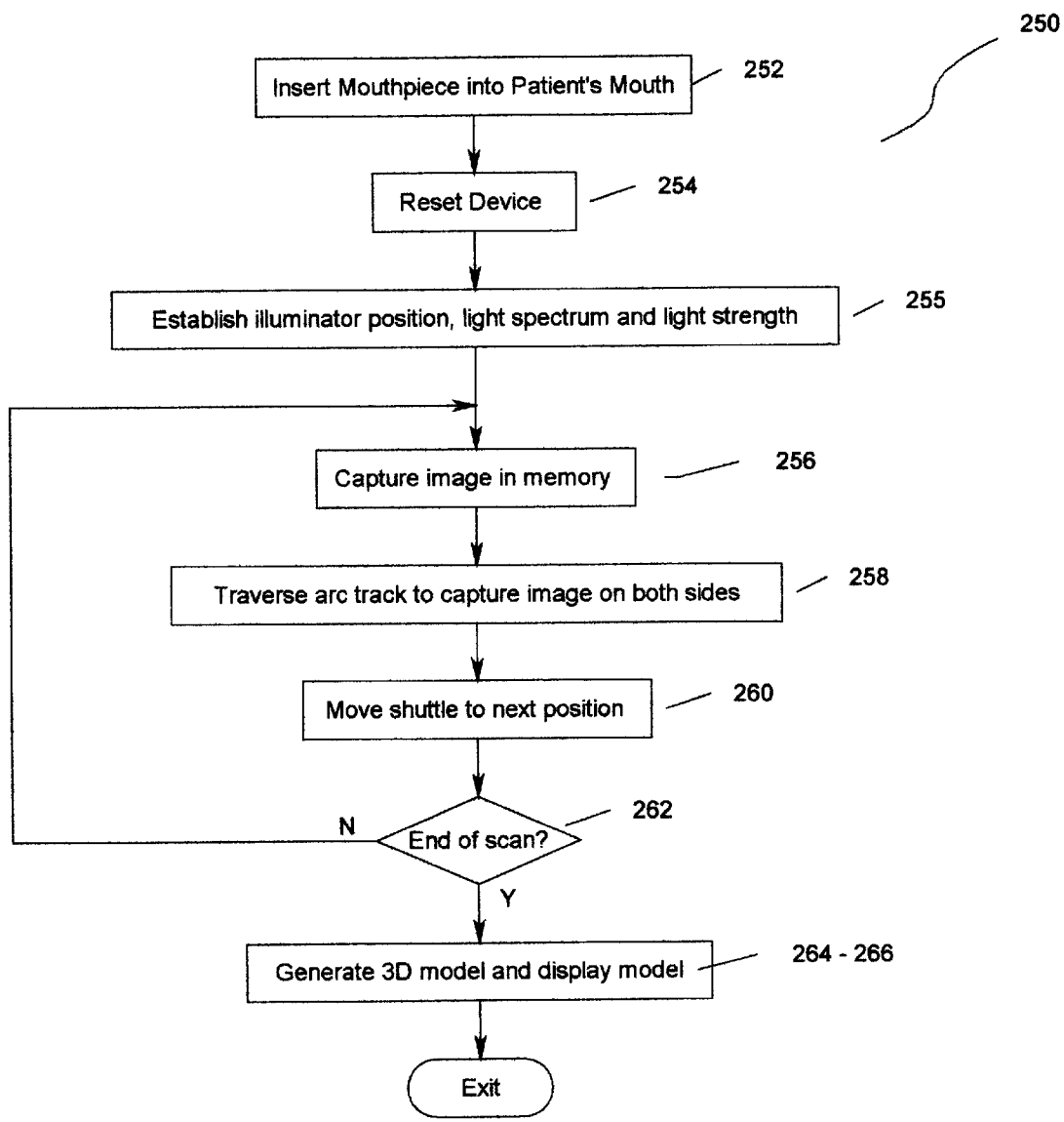
FIG. 4 illustrates a process in capturing images and generating 3D models from a patient.

FIG. 4 shows an exemplary process 250 for scanning and generating 3D models of dental structures. First, the mouthpiece 130 is inserted into the patient's mouth (step 252). Next, a reset operation is performed to move the shuttle 204 to an initial known position (step 254). The illuminator 134 position, light spectrum and light strength is established (step 255). The image processor 110 receives an image through the image aperture 132 and captures the image to its memory (step 256). The image processor 110 then instructs the image aperture 132 to traverse the arc track 210 over the dental structure to collect a sufficient number of images on both sides of the dental structure (step 258). The image processor 110 then actuates the drive mechanism 136 to move the shuttle 204 to the next incremental lateral position (step 260). At each lateral position, the image aperture 132 traverses the arc track 210 over the dental structure to collect a sufficient number of images on both sides of the dental structure before moving to the next lateral position. Next, the process 250 tests whether the shuttle 204 reaches the end of the patient's arch (step 262). If not, the process loops back to step 256 to continue the image acquisition operation. If the end has been reached, the process 250 generates a 3D model using the captured images (step 264) and displays the 3D model for review (step 266).

Figure 5:
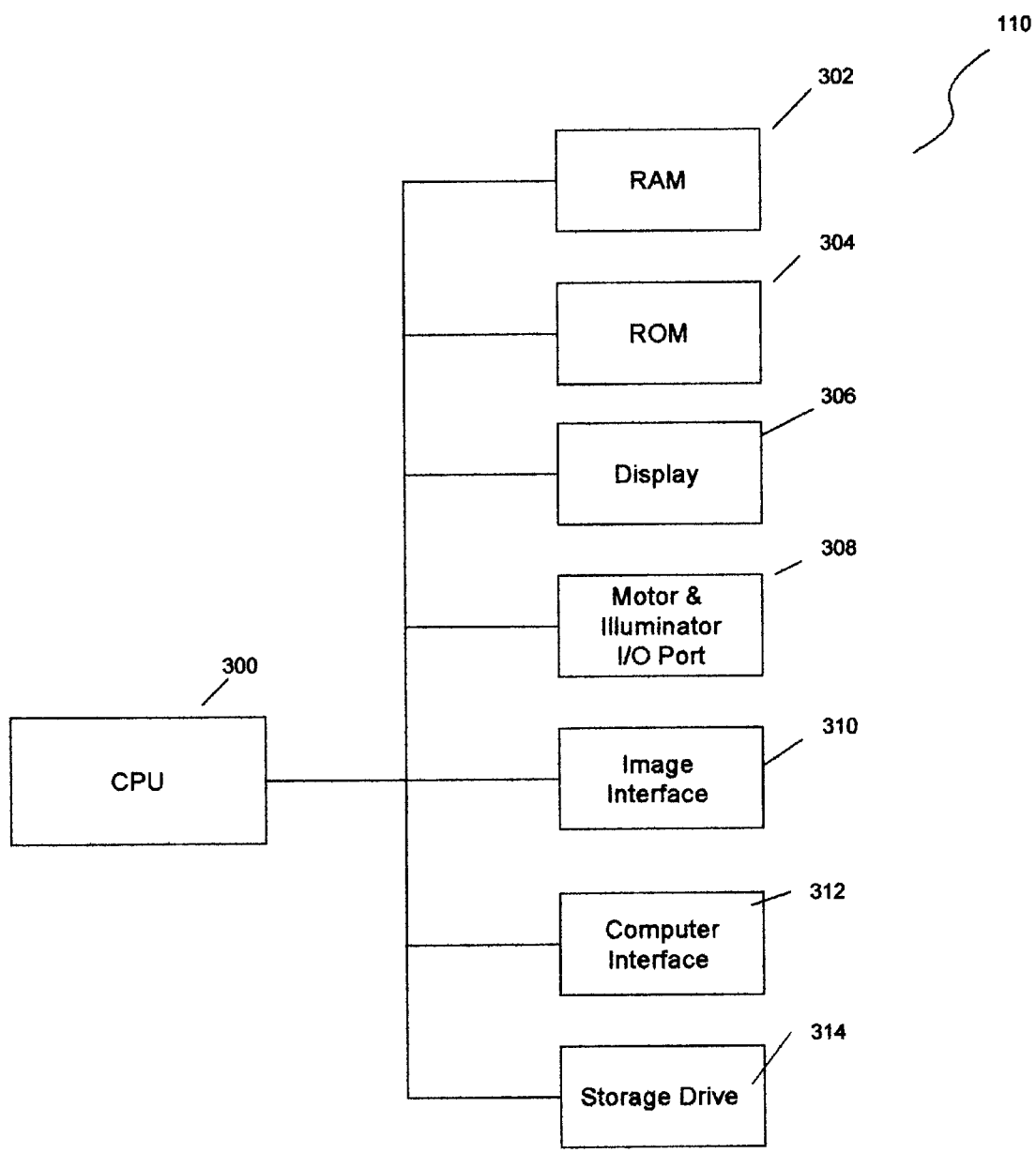
FIG. 5 shows an exemplary image processor for generating 3D models.

Turning now to FIG. 5, an exemplary image processor 110 is shown. The image processor 110 includes a central processing unit (CPU) 300, which can be a high performance CISC or RISC processor. The CPU 300 is connected to random access memory (RAM) 302 and read only memory (ROM) 304. The CPU 300 also is connected to a plurality of input/output devices, including a display 306, a motor input/output port 308 to drive the motor 136 (FIG. 1), an image interface 310 to receive image data from the scanner 100, and a computer interface 312. The CPU 300 can also be connected to a storage drive 312 such as a hard drive to store software and data and provides an interface for the communication of data with other equipment.

The CPU 300 executes code to control the image data acquisition and generate 3D models from the captured images. The captured images are processed with a pattern recognizer that maps various points of an object observed in the captured images, thereby obtaining the shape/contour information. In one implementation, 2D digitized images of the dental structures are output from the scanner 100 and stored in computer memory of the image processor 110 along with the positional information and illuminator settings. The stored images from a plurality of images obtained at different positions are then analyzed using stereometric methods to form a 3D view. This process is repeated for the complete set of captured images to create a full 3D model of the scanned dental structures in the oral cavity. The 3D model is then presented on a display or used in conjunction with a CAD/CAM system for patient diagnosis and treatment.

Figure 6:
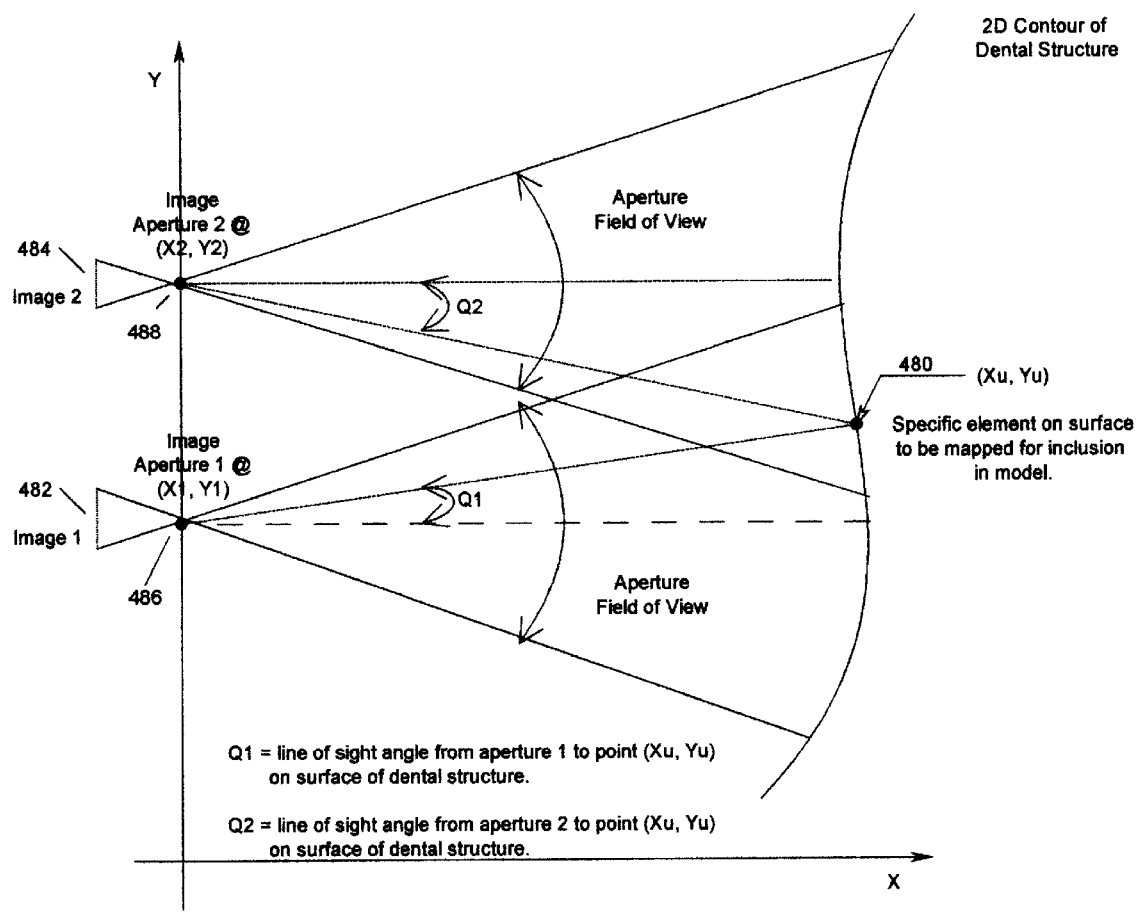
FIG. 6 shows an exemplary embodiment for modeling surface location and contour from stereo images.

FIG. 6 shows an exemplary embodiment for using stereo images to model the surface contour of dental structures. The example of FIG. 6 is described in terms of two-dimensions, but the process is readily extended to the third axis to derive three-dimensional surface contours for 3D models. With reference to FIG. 6, the following process is used to derive the position of a specific scene element 480 observed in images 482 and 484 captured through image apertures 486 and 488.

The image processor uses conventional image pattern matching techniques to identify a scene element that is observed in both image 482 and image 484. Further, based upon the image aperture field of view angle and the location of the specific scene element within the image sensor's array of pixels, the line of sight angle between the geometric plane of the image sensor and the scene element is derived. These line of sight angles are denoted in FIG. 6 as Q1 for an image aperture located at X1, Y1 and Q2 for an image aperture located at X2, Y2.

Let the as yet unknown coordinates for the location of the scene element of interest be denoted $x_u$ and $y_u$.

Based upon the geometry of the case of FIG. 6, $$y_u = (\tan Q1 \cdot x_u) + y_1$$

and $$\tan Q2 = (y_2 - y_u)/x_u$$

The value of $x_u$ and $y_u$ can now be solved using the above two equations and conventional techniques applicable to sets of linear equations. The stereometric method above can be generalized to add a third dimension $z_u$ and thereby derive a 3D surface contour or model of the imaged dental structure. The 3D version is based on differences in the line of sight angles projected into the third dimension to a dental structure element as viewed from at least two different aperture locations.

While for illustrative purposes this description is based upon the use of just two images, it is to be understood that the concept can be extended to more precisely find the 3D coordinates of a scene element by utilizing a multitude of images of the dental structure, taken from a multitude of image aperture positions and utilizing a multitude of illumination conditions.

In another implementation, image-processing operations based on triangulation can be used where beams of light are projected onto the dental structures and three-dimensional spatial locations are determined for points where the light reflects from the dental structure object. As the reflected light bounces off the object at an angle relative to the known location and bearing of the light source, the system collects the reflection information from a known location relative to the light source and then determines the coordinates of the point or points of reflection by triangulation. A single dot system projects a single beam of light which, when reflected, produces a single dot of reflection. A scan line system beams a plane of light against the dental structure and which is reflected as a curvilinear-shaped set of points describing one contour line of the object. The location of each point in that curvilinear set of points can be determined by triangulation. The system projects a light plane (i.e., a laser stripe) from a known location and reads the reflection of multiple points depicting the contour of the dental structure at a location distant from the camera and from which the position can be triangulated.

In addition to optical triangulation systems, other alternative optical scanning systems can be used, including range meters systems. Range meter systems typically use an infrared-pulsed laser and mechanical scanning techniques to project a dot laser across an object and then measure the phase delay of the reflected signal.

Once the dental structure coordinates have been scanned, the system removes redundant points and generates a 3D model from the scanned data using various techniques known in the art. In one embodiment the process examines data for two adjacent laser stripes. Next, the process sweeps through each Y coordinate from the top of the two laser stripes to the bottom of the two stripes and creates triangles for the geometric 3D model. When the process has reached the bottom of the stripes, the triangulating process for the current laser stripes is finished and the next set of adjacent scan lines are retrieved until a triangulated mesh covering the whole dental structure is generated. Once the mesh has been generated, a 3D model with realistic shading and lighting can be generated.

Figure 7:
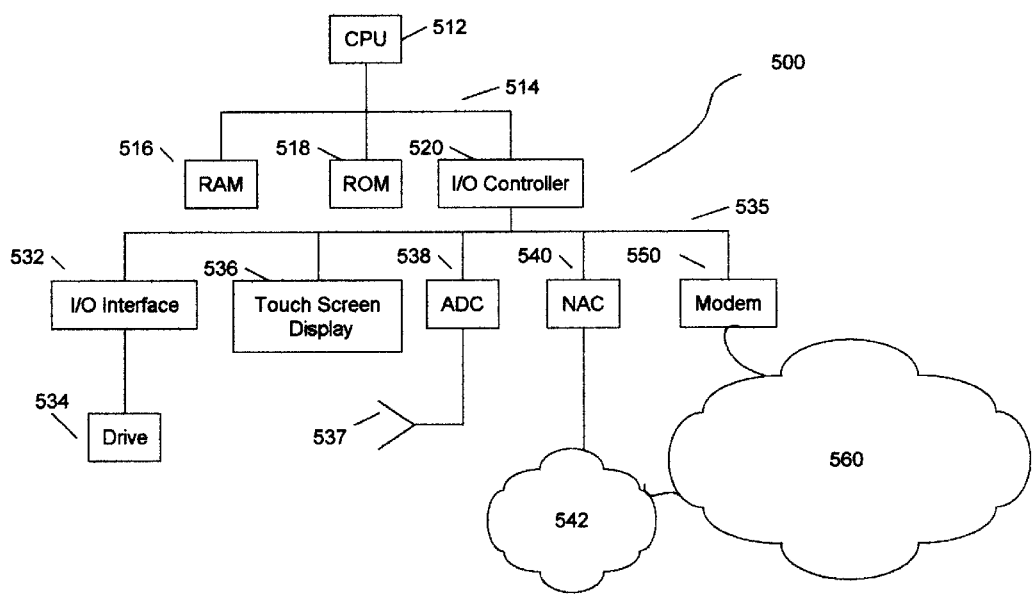
FIG. 7 shows an exemplary computer for using the 3D models.

FIG. 7 shows an exemplary computer 500 for processing dental image data and for generating 3D models. The system 500 includes a processor (CPU) 512, RAM 516, ROM 518 and an I/O controller 520 coupled by a CPU bus 514. The I/O controller 520 is also coupled to an I/O bus 535. The I/O bus 535 communicates with an I/O interface 532 that in turn controls a solid state drive (flash RAM) 534 or a removable disk drive. The I/O bus 535 is also connected to input devices such as a touch-screen display 536. In place of, or in parallel with the touch-screen display 536, a keypad can be connected to the I/O bus 535 to receive user data entry. Alternatively, voice recognition can be used in conjunction with and/or replace the touch-screen display 536 or keypad. In such an embodiment, a microphone 537 is connected to an analog to digital converter (ADC) 538 that interfaces with the processor 512.

A network access card 540 can be connected to the I/O bus 535 to allow the computer 500 access to a network 542. Through the network 542, or through a modem 550 connected to the I/O bus 535, the computer 500 can access a wide area network 540 such as the Internet. An Internet community with one or more service providers or marketers is connected to the network. The Internet community can provide value added services such as services to create a physical teeth model from the 3D model.

The above system supports a rapid imaging of dental structures in such a way, and with sufficient resolution such that the acquired images can be processed into accurate 3D models of the imaged dental structures. The images and models can be processed on the computer 500 to provide dental diagnosis and to support the specification and manufacture of dental prosthetics such as bridgeworks, crowns or other precision moldings and fabrications. The computer 500 can transmit data representing a set of dental images and models over a wide area network such as the Internet to support activity such as professional consults or insurance provider reviews and the images and models may be electronically archived for future reference.

Although an illustrative embodiment of the present invention, and various modifications thereof, have been described in detail herein with reference to the accompanying drawings, it is to be understood that the invention is not limited to this precise embodiment and the described modifications, and that various changes and further modifications may be effected therein by one skilled in the art without departing from the scope or spirit of the invention as defined in the appended claims.

What is claimed is:

1. A method for optically imaging a dental structure within an oral cavity, comprising:

capturing one or more images of the dental structure through at least one image aperture with a multi-dimensional camera coupled to the image aperture, the image aperture movably coupled to an intra-oral track; and generating a three-dimensional (3D) model of the dental structure based on the images captured by the image aperture.

2. The method of claim 1, further comprising moving the image aperture incrementally or continuously within the oral cavity.

3. The method of claim 2, further comprising actuating a motor to move the image aperture incrementally or continuously within the oral cavity.

4. The method of claim 1, wherein the intra-oral track is arch-shaped.

5. The method of claim 1, further comprising providing an illuminator movably mounted on the intra-oral track to illuminate the dental structure.

6. The method of claim 5, further comprising moving the illuminator incrementally or continuously within the oral cavity.

7. The method of claim 1, wherein generating a three-dimensional model further comprises performing stereometric analysis on the captured images.

8. The method of claim 1, wherein generating a three-dimensional model further comprises performing a scanning illumination beam and triangulation analysis on the captured images.

9. The method of claim 1, further comprising displaying a representation of said 3D model.

10. The method of claim 1, further comprising transmitting the 3D model over a network.

11. The method of claim 1, further comprising diagnosis and treatment of a patient using the 3D model.

12. A system to optically image a dental structure within an oral cavity, comprising:
an intra-oral track adapted to be inserted inside the oral cavity;
at least one image aperture movably coupled to the intra-oral track and adapted to capture one or more images of the dental structure;
a multi-dimensional camera coupled to the image aperture; and
an image processor coupled to the image aperture to generate a three-dimensional (3D) model of the dental structure based on the images captured by the image aperture.

13. The system of claim 12, wherein the image aperture is either incrementally or continuously moved on the track.

14. The system of claim 12, further comprising a motor coupled to the image aperture to move the image aperture incrementally or continuously within the oral cavity.

15. The system of claim 12, wherein the intra-oral track is arch-shaped.

16. The system of claim 12, further comprising one or more illuminators movably mounted on the intra-oral track to illuminate the dental structure.

17. The system of claim 16, wherein each illuminator is incrementally or continuously moved within the oral cavity.

18. The system of claim 12, wherein the image processor further comprises a stereometric processor.

19. The system of claim 12, wherein the image processor scans an illumination beam and performs triangulation analysis on the captured images to generate a three-dimensional model.

20. The system of claim 12, further comprising a display coupled to the image processor to show a representation of said 3D model.

21. The system of claim 12, wherein the image processor is coupled to a network to transmit the 3D model to a remote system.

22. The system of claim 12, wherein the camera is a two-dimensional camera.

23. The system of claim 12, wherein the camera is adapted to be mounted inside the oral cavity.

24. The system of claim 12, wherein the camera is adapted to be mounted outside the oral cavity.

25. A system to optically image a dental structure within an oral cavity, comprising:
an intra-oral track adapted to be inserted inside the oral cavity;
a plurality of image apertures movably coupled to the intra-oral track and adapted to capture one or more images of the dental structure;
a multi-dimensional camera coupled to the image aperture; and
an image processor coupled to the image apertures to generate a three-dimensional (3D) model of the dental structure based on the images captured by the image apertures.

* * * * *